(12) United States Patent
Wing et al.

(10) Patent No.: US 6,409,220 B1
(45) Date of Patent: Jun. 25, 2002

(54) UNIVERSAL SUCTION CANISTER POUR SPOUT ADAPTOR

(75) Inventors: Daniel M. Wing, Utica; John Sutherland, New Hartford; Stephen J. Scheuermann, Oneida, all of NY (US)

(73) Assignee: ConMed Corporation, Utica, NY (US)

( * ) Notice: Subject to any disclaimer, the term of this patent is extended or adjusted under 35 U.S.C. 154(b) by 80 days.

(21) Appl. No.: 09/665,028

(22) Filed: Sep. 19, 2000

(51) Int. Cl.⁷ .................. F16L 55/00; A61M 25/00; B01D 63/00
(52) U.S. Cl. ............... 285/12; 285/901; 285/148.23; 285/133.11; 285/131.1; 604/284; 604/256; 220/287; 128/912; 215/228; 215/319; 138/89
(58) Field of Search .................. 285/12, 901, 148.18, 285/148.23, 131.1, 132.1, 133.11, 133.3; 604/284, 278, 256, 905; 220/287; 128/912; 215/228, 319, DIG. 3; 138/89

(56) References Cited

U.S. PATENT DOCUMENTS

| | | | |
|---|---|---|---|
| 3,655,089 A | | 4/1972 | Tower |
| 3,741,217 A | * | 6/1973 | Ciarico ........................ 128/912 |
| 4,207,894 A | | 6/1980 | Klibansky |
| 4,342,337 A | * | 8/1982 | Underwood .................. 138/89 |
| 4,661,110 A | * | 4/1987 | Fortier et al. ............... 604/256 |
| 4,668,225 A | * | 5/1987 | Russo et al. ................. 604/264 |
| 4,828,546 A | | 5/1989 | McNeil |
| 4,874,365 A | * | 10/1989 | Frederick ..................... 604/284 |
| 5,087,250 A | | 2/1992 | Lichte |
| 5,098,405 A | * | 3/1992 | Peterson ...................... 604/256 |
| 5,254,080 A | | 10/1993 | Lindsay |
| 5,267,983 A | * | 12/1993 | Oilschlager et al. ......... 604/256 |
| 5,382,242 A | * | 1/1995 | Horton et al. ............... 604/284 |
| 5,385,372 A | * | 1/1995 | Utterberg ..................... 285/901 |
| 5,399,156 A | | 3/1995 | Lindsay |
| 5,399,173 A | * | 3/1995 | Parks et al. ............. 285/148.23 |
| 5,413,561 A | * | 5/1995 | Fischell et al. .............. 604/256 |
| 5,588,958 A | | 12/1996 | Cunningham |
| 5,665,080 A | | 9/1997 | Vandenberg |
| 5,674,209 A | * | 10/1997 | Yarger ......................... 285/901 |
| 5,741,237 A | | 4/1998 | Walker |
| 5,944,238 A | | 8/1999 | Stark |
| 5,954,957 A | | 9/1999 | Chin-Loy |

* cited by examiner

*Primary Examiner*—Eric K. Nicholson
(74) *Attorney, Agent, or Firm*—George R. McGuire; Hancock & Estabrook, LLP

(57) ABSTRACT

A universal suction canister pour spout adaptor for use with suction canisters of various designs to fit onto the internal or external pour spout of various standard suction canisters so that such canisters can receive materials through their pour spouts during surgical procedures. The suction canister adaptor has a series of stepped external and internal diameters sized for engaging the various sized pour spouts of various suction canisters.

10 Claims, 2 Drawing Sheets

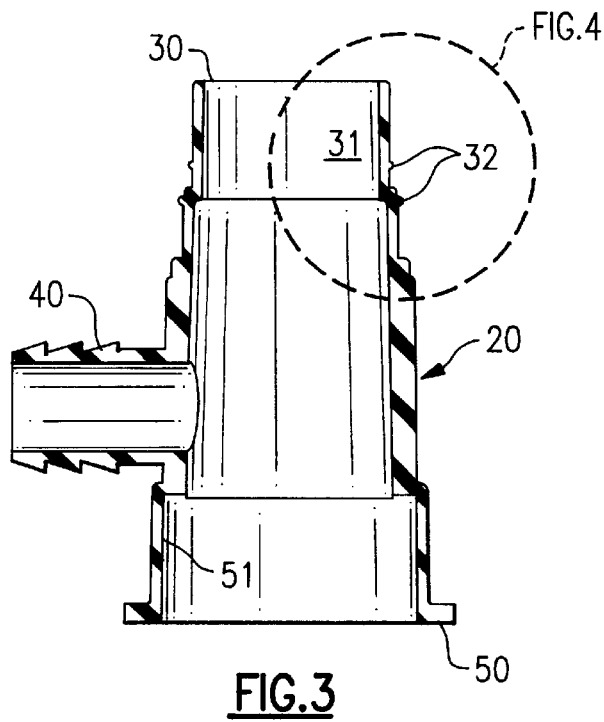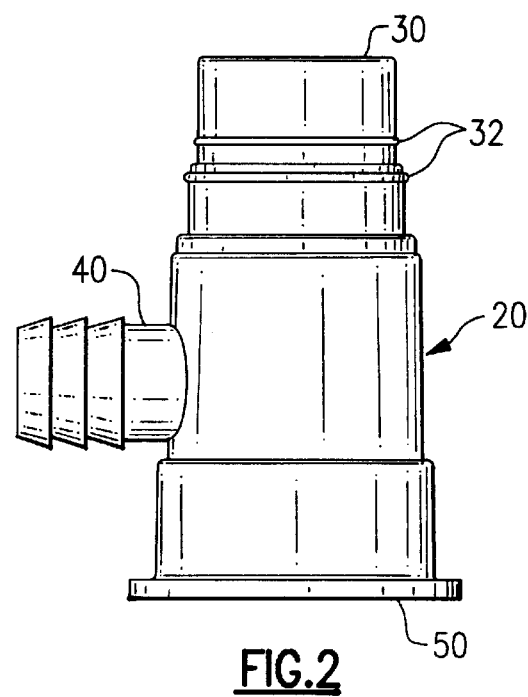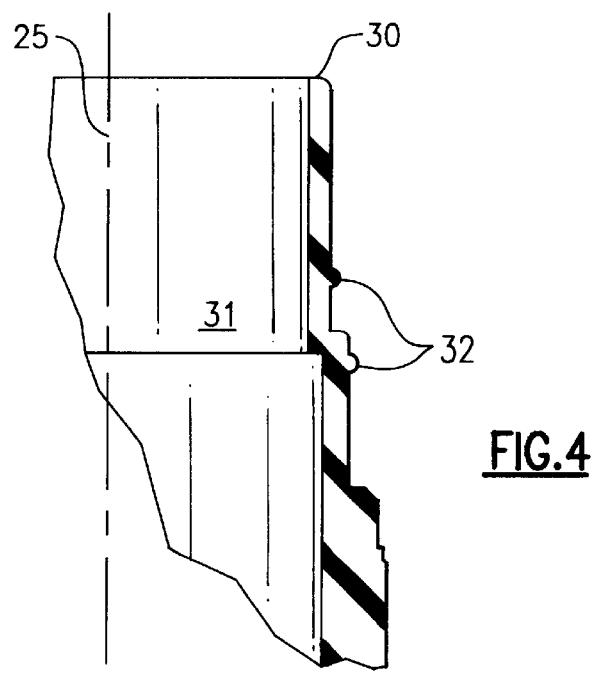

UNIVERSAL SUCTION CANISTER POUR SPOUT ADAPTOR

TECHNICAL FIELD

This invention relates in general to a universal pour spout adaptor for use with suction canisters of various designs and, in particular, to such an adaptor that will fit onto the pour spout of various standard suction canisters so that such canisters can receive materials through their pour spouts during medical procedures.

BACKGROUND ART

During the performance of various medical procedures it frequently becomes necessary to remove material such as vomitus during an emergency, or bone chips during an orthopedic procedure, by suctioning. The suction canisters used in medical procedures have standard fittings for receiving suction tubing, typically 1/8" to 9/32" ID. However, in some medical procedures, as discussed above, the nature of the materials being removed by the suctioning are such that the materials would clog the standard tubing and fittings used for connecting suction tubing. Accordingly, the only other opening on most suction canisters is the pour spout through which the container is emptied.

However, there is no industry standard for suction canister pour spouts, so any device which is intended to provide a secure, air-tight connection between large ID suction tubing and the pour spouts of the various suction canisters must be designed to accommodate several different styles of pour spouts. Some suction cannister pour spouts have protrusions on the inside of the container that make air tight connection to the interior of the cannister difficult. With such suction canisters it is necessary to connect a large ID suction tubing to the exterior of the canister pour spout. With other canisters, the exterior pour spout is too short to form a solid connection, or the variation in the OD's is such that an impractically long adapter would be required. With suction canisters of these designs, a connection to the interior of the pour spout becomes necessary.

The present invention is designed to overcome one or more of these problems.

BRIEF DESCRIPTION OF THE DRAWINGS

FIG. 2 is a side elevational view of the body portion of the pour spout adaptor to better illustrate the construction thereof;

FIG. 3 is a cross-sectional view of the pour spout adaptor body portion illustrated in FIG. 2;

FIG. 4 is an enlarged portion of FIG. 3 to better illustrate a portion of the construction thereof.

BEST MODE FOR CARRYING OUT THE INVENTION

Figure 1:
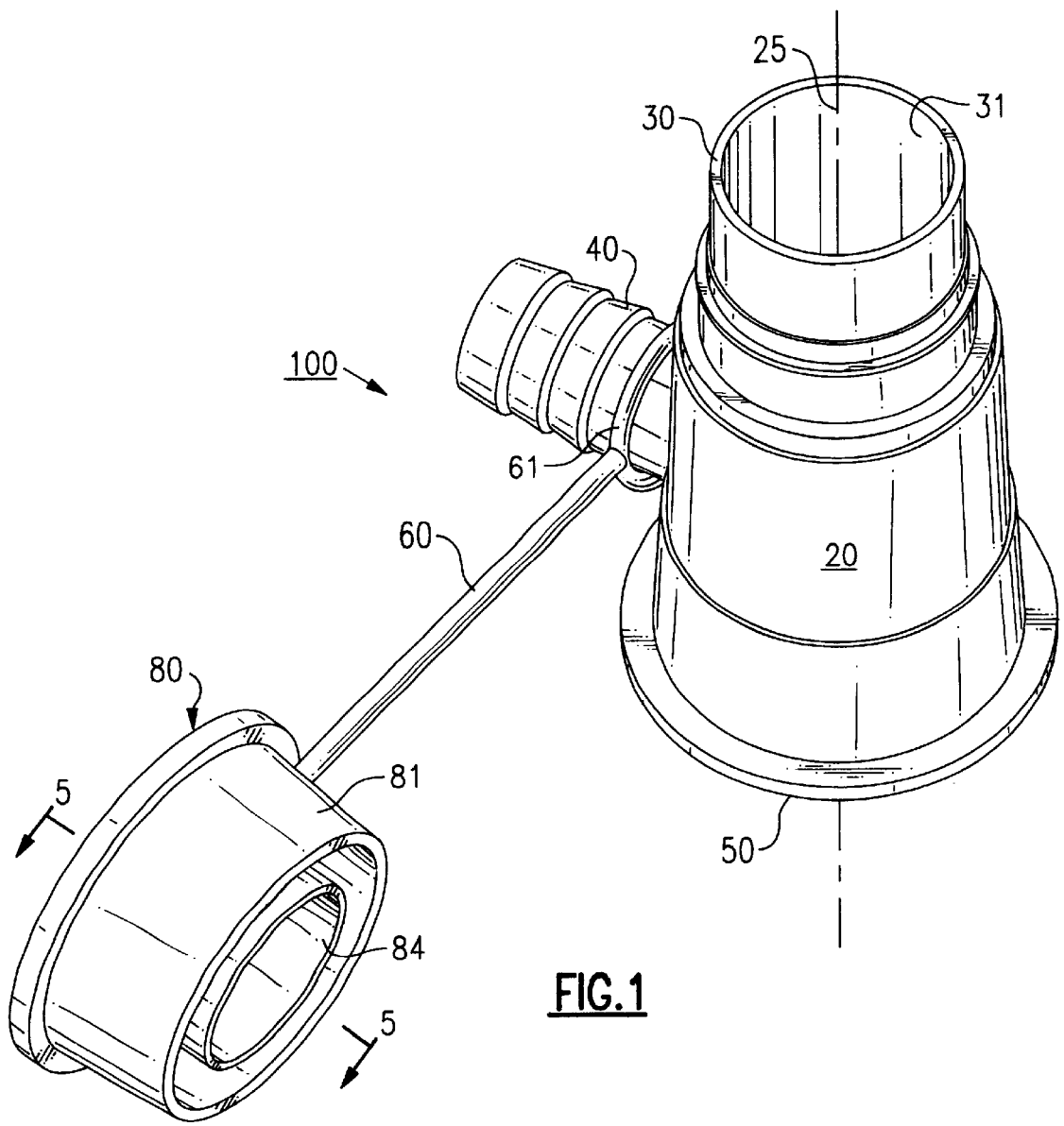
FIG. 1 is a perspective view of the suction canister pour spout adapter of the present invention including the cap portion connected to the body portion by a tether.
Figure 5:
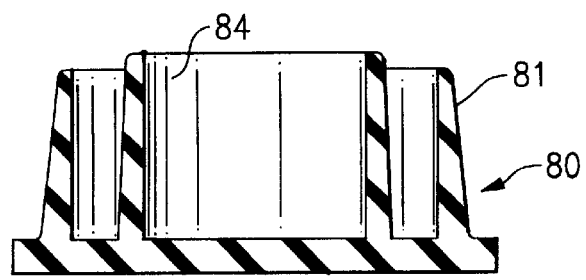
FIG. 5 is a cross-sectional view of the pour spout adaptor cap portion to better illustrate the internal construction thereof.

Referring now to FIG. 1, there is shown a suction canister pour spout adaptor 100 constructed in accordance with the present invention. The adaptor 100 includes a body portion 20 and a cap portion 80 which is preferably joined to the body portion 20 by a tether 60, although the use of a tether 60 is for convenience of use, and not to be considered a necessary requirement of the invention.

To enable the pour spout adaptor 100 to be used with various suction canisters, the body portion 20 is formed as a hollow tube. The outer diameter of the body portion 20 is stepped so that one end thereof 30, referred to for convenience of illustration as the "upper end" with reference to the orientation of the drawings, is insertable into a suction cannister pour spout to engage an internal diameter of the pour spout. To ensure proper sealing and structural support of the adapter 100 with the internal diameter of a suction canister, the stepped portions on the outer diameter of the upper end 30 of the body portion 100 are tapered inwardly, towards a longitudinal axis 25 of the adaptor 100, in a direction towards the open end thereof. In this manner, when the upper end 30 of the body portion is inserted into the suction canister pour spout, the stepped portions become increasingly greater as they are passed through the suction canister pour spout opening until a proper seal is formed by engagement of one of the stepped portions with the pour spout opening. To facilitate a locking seal between this portion of the adapter 100 and the suction canister pour spout, locking rings 32 are provided over which a lip on the opening of the suction canister pour spout passes to better secure and retain the end 30 within the pour spout.

The opposite end 50 of the body portion 20, referred to as the "lower end", has the internal diameter thereof stepped to receive the external diameter of a suction cannister pour spout. In this manner the body portion 20 may be used to form a sealing engagement with a suction canister pour spout using either end, 30 or 50, of the body portion 20, whichever is the most suitable for the particular pour spout with which the adaptor 100 is to be used. To this end, the inner surfaces of the lower end 50 of the body portion 20 are also tapered inwardly towards the longitudinal centerline 25 of the body portion 20 from the open end thereof so that the internal diameter of these stepped portions also becomes increasingly smaller as the external diameter of a suction canister pour spout is inserted into the opening in the lower end 50 of the adapter 100.

To connect the pour spout adaptor 100 to a source of material which is to be drawn into the suction canister, a hollow barbed suction tube fitting 40 is coupled to the body portion 20 between the upper 30 and lower 50 ends thereof so that the interior of the body portion 20 forms a discharge connection with the cannister pour spout through which the materials removed by suctioning can be drawn through the fitting 40 and discharged into the suction cannister. Because the body portion 20 is formed as a hollow tube, the end of the adapter 100 which is not forming a seal with the suction canister pour spout must be closed so that the suction will be transferred to the tube and the materials removed by suctioning will be discharged into the suction canister. To this end a cap 80 is provided which is engageable with both of the open ends 30 and 50 of the body portion 20, the upper end and the lower end, respectively.

The cap 80 is sized such that the external diameter thereof 81 will sealingly engage the largest internal diameter 51 of the lower end 50, and the external diameter of a concentric cylinder 84 carried within the cap 80 will sealingly engage the smallest internal diameter 31 of the upper end 30. In this manner, when the cap 80 is placed on either end 30 or 50 of the body portion 20, a seal is formed closing the end upon which the cap 80 is mounted and permitting a suction to be drawn only through the uncapped end.

To facilitate the availability of the cap 80 for connection to the body portion 20, a flexible tether 60 is connected to the cap 80 and extends a suitable length to permit the cap 80 to engage both ends 30 and 50 of the body portion. A closed loop 61 is preferably formed at an opposite end of the tether 60 for engaging the barbed fitting 40 to facilitate removal when desired.

While stepped external diameters of various sizes may be formed on both the upper end 30 of the body portion 20, and stepped internal diameters of various sized may be formed on the lower end 50, in the preferred embodiment of the suction canister pour spout adapter 100, it has been found that four external diameters of 0.880", 0.900", 0.980" and 1.093", on the upper end 30, and two internal diameters of 1.168" and 1.113" on the lower end 50, are useful for a wide range of suction canisters.

While this invention has been described in the specification and illustrated in the drawings with reference to a preferred embodiment, the structure of which has been disclosed herein, it will be understood by those skilled in the art to which this invention pertains that various changes may be made, and equivalents may be substituted for elements of the invention without departing from the scope of the claims. Therefore, it is intended that the invention not be limited to the particular embodiment disclosed in the specification and shown in the drawings as the best mode presently known by the inventor(s) for carrying out this invention, nor confined to the details set forth, but that the invention will include all embodiments, modifications and changes as may come within the scope of the following claims:

What is claimed is:

1. A universal adaptor for engaging the pour spout of a suction canister to enable materials to be drawn into the canister through the pour spout, comprising:
    a housing for receiving materials to be drawn into a suction canister for disposal;
    said housing having a first end and a second end coaxial about a longitudinal axis and defining an opening in said housing between said first end and said second end through said housing extending along said longitudinal axis;
    said first end of said housing having a plurality of external diameters stepped in increasing diameters inwardly from said first end opening;
    said second end of said housing having a plurality of internal diameters stepped in decreasing diameters inwardly from said second end opening;
    an input port carried by said housing between said first end and said second end for coupling to a source of material to be drawn into said housing; and
    a closure adapted to mutually exclusively close one of said first end or said second end so that materials drawn through said input port can be drawn through said housing and discharged into a suction canister to which the adaptor is engaged.

2. The universal adaptor of claim 1 further including a tether attached to said closure and said housing to facilitate attachment of said closure to said fist end or said second end of said housing.

3. The universal adaptor of claim 1 wherein said closure includes concentric first and second cylinders;
    said first cylinder having a diameter for engagement with said first end for forming a closure thereof, and said second cylinder having a diameter for engagement with said second end for forming a closure thereof.

4. The universal adaptor of claim 1 wherein said first end of said housing is formed with at least four stepped external diameters.

5. The universal adaptor of claim 1 wherein said second end of said housing is formed with at least two internal stepped diameters.

6. The universal adaptor of claim 2 wherein said tether is removably securable to said housing.

7. The universal adaptor of claim 1 further including at least one locking ring encircling said first end forming a retainer to facilitate retaining the adaptor inside a pour spout of a suction canister.

8. The universal adaptor of claim 4 wherein said four stepped external diameters are approximately 0.880"; approximately 0.900"; approximately 0.980"; and approximately 1.093", respectively.

9. The universal adaptor of claim 5 wherein said two internal stepped diameters are approximately 1.168" and approximately 1.113", respectively.

10. The universal adaptor of claim 1 wherein
    said first end of said housing is formed with at least four stepped external diameters of approximately 0.880"; approximately 0.900"; approximately 0.980"; and approximately 1.093", respectively; and
    said second end of said housing is formed with at least two stepped internal diameters of approximately 1.168" and approximately 1.113", respectively.

* * * * *